US012796935B2

United States Patent

(12) United States Patent
Patwardhan et al.
(10) Patent No.: US 12,796,935 B2
(45) Date of Patent: Nov. 17, 2026

(54) MULTI-MODAL SKIN IMAGING

(71) Applicant: Canfield Scientific, Incorporated, Parsippany, NJ (US)

(72) Inventors: Sachin V. Patwardhan, Mount Tabor, NJ (US); Daniel E. DiGregorio, Fairfield, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 104 days.

(21) Appl. No.: 18/568,805

(22) PCT Filed: Jun. 14, 2022

(86) PCT No.: PCT/US2022/033494
§ 371 (c)(1),
(2) Date: Dec. 9, 2023

(87) PCT Pub. No.: WO2022/266145
PCT Pub. Date: Dec. 22, 2022

(65) Prior Publication Data

US 2024/0268678 A1 Aug. 15, 2024

Related U.S. Application Data

(60) Provisional application No. 63/212,339, filed on Jun. 18, 2021.

(51) Int. Cl.
*A61B 5/00* (2006.01)
*G01N 21/17* (2006.01)
(Continued)

(52) U.S. Cl.
CPC ............ *A61B 5/0077* (2013.01); *A61B 5/444* (2013.01); *G01N 21/474* (2013.01);
(Continued)

(58) Field of Classification Search
CPC ..... A61B 5/0077; A61B 5/444; A61B 5/0071; G01N 21/474; G01N 2021/1765;
(Continued)

(56) References Cited

U.S. PATENT DOCUMENTS

2004/0185552 A1* 9/2004 Griner .................... G01N 21/78
435/286.1
2008/0194928 A1* 8/2008 Bandic ................... A61B 5/443
600/306
(Continued)

FOREIGN PATENT DOCUMENTS

WO 2020123722 A1 6/2020

*Primary Examiner* — Dominic J Bologna

(57) ABSTRACT

Apparatuses and methods are disclosed for capturing and analyzing images of tissue, such as human skin, using multiple modalities. Exemplary devices are described having a detection polarizer via which an area of tissue is imaged and one or more light sources whose emitted light is polarized with a source polarizer. In exemplary operation, an area of tissue can be imaged as the illumination emitted from an exemplary device is varied among plain white, polarized white, and light of one or more bands of wavelengths, such as narrow-band blue, for fluorescence imaging of one or more fluorophores. In further implementations, absorption imaging can be carried out with cross-polarized narrow-band illumination.

20 Claims, 9 Drawing Sheets

(51) Int. Cl.
*G01N 21/47* (2006.01)
*G02B 21/00* (2006.01)
*G02B 21/08* (2006.01)
*G02B 21/16* (2006.01)

(52) U.S. Cl.
CPC ....... *G02B 21/0008* (2013.01); *G02B 21/084* (2013.01); *A61B 5/0071* (2013.01); *G01N 2021/1765* (2013.01); *G01N 2021/4759* (2013.01); *G01N 2021/4792* (2013.01); *G01N 2201/0626* (2013.01); *G01N 2201/0627* (2013.01); *G02B 21/16* (2013.01)

(58) Field of Classification Search
CPC ... G01N 2021/4759; G01N 2021/4792; G01N 2201/0626; G01N 2201/0627; G02B 21/0008; G02B 21/084; G02B 21/16
See application file for complete search history.

(56) References Cited

U.S. PATENT DOCUMENTS

| | | | | |
|---|---|---|---|---|
| 2009/0131800 | A1 | 5/2009 | Liang | |
| 2009/0181339 | A1* | 7/2009 | Liang | A61B 1/24 433/29 |
| 2011/0031894 | A1 | 2/2011 | Van De Ven | |
| 2020/0193580 | A1* | 6/2020 | McCall | G06T 7/55 |
| 2020/0240918 | A1* | 7/2020 | Wilzbach | G01N 21/6458 |
| 2020/0375466 | A1* | 12/2020 | Ras | A61B 5/0077 |
| 2023/0417979 | A1* | 12/2023 | Haag | G02F 1/13362 |

* cited by examiner

AS-CAPTURED IMAGE

ENHANCED IMAGE WITHOUT BLUE CHANNEL

AS-CAPTURED IMAGE

ENHANCED IMAGE WITHOUT BLUE CHANNEL

MULTI-MODAL SKIN IMAGING

RELATED APPLICATIONS

This Application is a U.S. National Phase filing of International Patent Application No. PCT/US2022/033494 filed Jun. 14, 2022, which claims priority from U.S. Provisional Patent Application No. 63/212,339 filed Jun. 18, 2021. Each of the aforementioned applications is incorporated herein by reference in its entirety.

BACKGROUND INFORMATION

The present disclosure relates to the imaging of tissue, such as skin.

Various skin features are best imaged with different modalities, such as parallel-polarized imaging for superficial features like wrinkles and lines, cross-polarized imaging for sub-surface features like pigmentation and vasculature, and fluorescence imaging for skin lesions such as keratoses and carcinomas characterized by the presence of certain fluorophores, such as fluorescing microgranularity, scale, and globular structures, typical of seborrheic keratoses (SK), actinic keratoses (AK), and squamous cell carcinomas (SCCs), respectively. In addition to the aforementioned specialized modalities, unpolarized white light imaging is also useful, to capture standard white light images of skin, as it would appear to the naked eye.

In addition to such enhanced and standard imaging capabilities, users of skin imaging devices also demand convenience and portability, with a preference for devices having a compact form factor. Such compactness, however, limits the amount of space available for such things as: multiple different illumination sources, with different emission spectra; multiple polarizers, for illumination and detection; multiple filters; and mechanisms to selectively move the polarizers and/or filters into and out of their active positions to effect the various imaging modalities.

There is a need, therefore, for skin imaging devices that can satisfy such competing considerations, such as capabilities and compactness, as discussed above.

SUMMARY OF THE DISCLOSURE

A skin imaging apparatus that is capable of multiple imaging modes is disclosed. In exemplary implementations, an imaging apparatus is provided that is configured to selectively operate in one of several imaging modes, including white light illumination without polarization; white light illumination with cross-polarization; and fluorescence imaging with narrow-band, visible light illumination. In exemplary implementations, such an illumination may be a blue illumination, among other possibilities. Other modes may include fluorescence imaging with more than one narrow-band illumination for imaging multiple different fluorophores, and absorption imaging for one or more compounds.

In exemplary implementations, an imaging apparatus in accordance with the present disclosure is provided as a dermatoscope or as an attachment thereto, or as an attachment to a camera or mobile device with an integrated camera, such as a smartphone or tablet computer, among other possibilities.

These and other aspects of such apparatuses and methods and exemplary variants thereof are described in greater detail below.

BRIEF DESCRIPTION OF THE DRAWINGS

A more complete understanding of the present disclosure may be realized by reference to the accompanying drawings.

DETAILED DESCRIPTION

Figure 1:
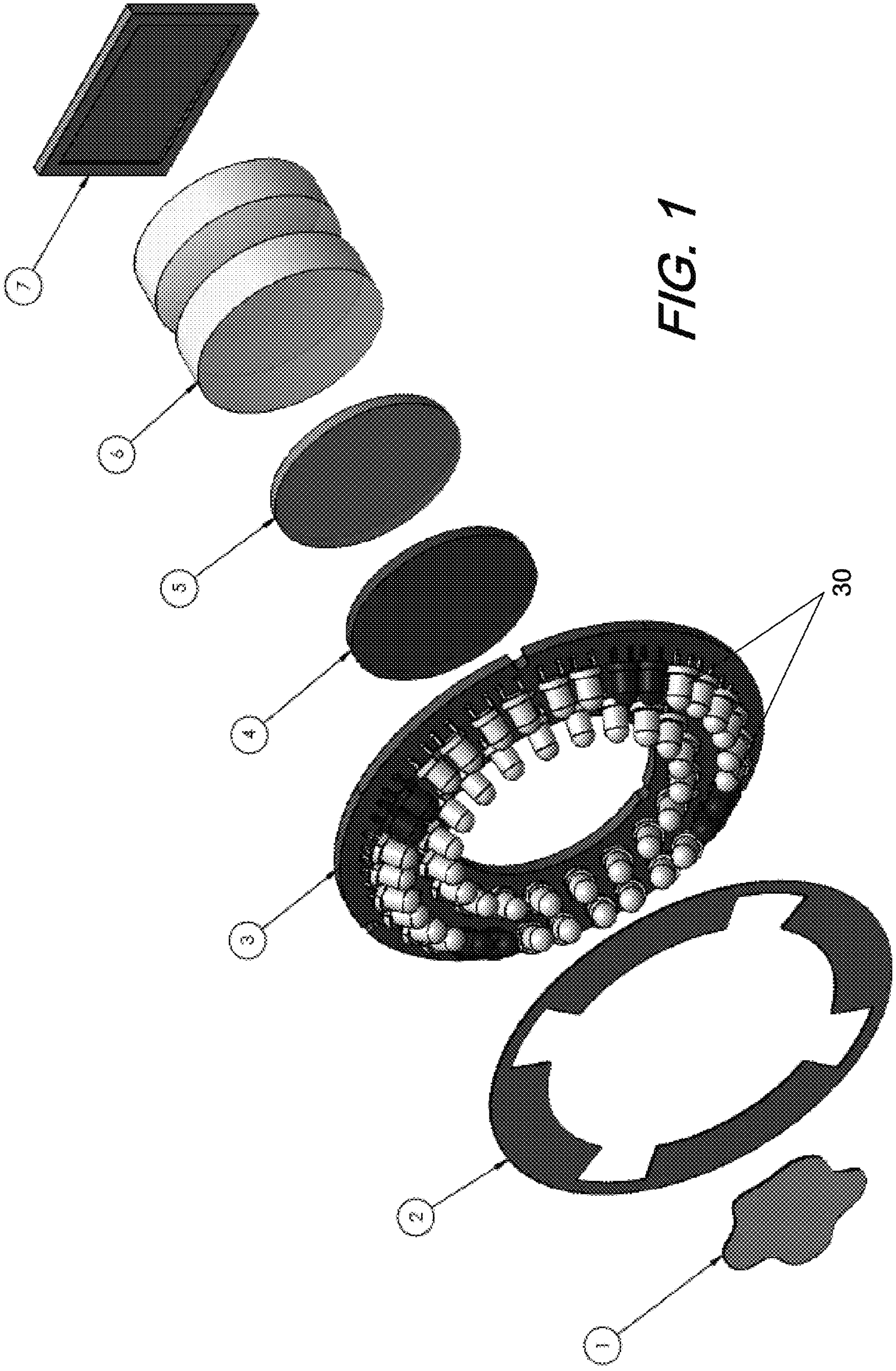
FIG. 1 is an exploded view of various elements of an exemplary imaging arrangement in accordance with the present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures, and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the drawings herein represent conceptual views of illustrative structures embodying the principles of the disclosure.

In addition, it will be appreciated by those skilled in art that any flowcharts, flow diagrams, and the like represent various processes which may be substantially represented in a computer readable medium and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software. When provided by a processor, the functions may be provided by a dedicated processor, by a shared processor, or by a plurality of processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture and a 3D volumetric image data might represent a stack of 2D images that represent a 3D volume of the object being imaged, such as a stack of MRI images. The term "image" as used herein may also refer to the results of processing one or more captured images to derive a further image.

Exemplary implementations of a device capable of operating in multiple imaging modes will now be described. A first imaging mode is useful for capturing standard, white-light images of skin, as it would appear to the naked eye. A second imaging mode allows for the capture of white-light cross-polarized images of skin, in which superficial and specular reflectance from the air/tissue interface is reduced, while allowing some subsurface details (such as lesion boundaries, micro-vascular patterns, etc.) to be imaged. A third imaging mode, such as with a blue illumination, is useful for imaging skin lesions, particularly non-melanocytic lesions, such as, for example, actinic keratoses (AK), seborrheic keratoses (SK), basal cell carcinomas (BCC), and squamous cell carcinomas (SCC). Such lesions have distinct patterns that can be seen with blue fluorescence imaging, facilitating their identification and differentiation. Descriptions of further implementations of apparatus capable of different and/or additional modes of operation will follow.

FIG. 1 is an exploded isometric view of various elements of an exemplary imaging arrangement in accordance with the present disclosure. In the arrangement of FIG. 1, an imaging target 1 can be viewed by an image capture element 7, such as a CCD sensor of a camera, via elements 2-6 arranged along an optical path between the target 1 and the image capture element 7. In the exemplary arrangement shown, element 2 is a polarizer, also referred to herein as source polarizer 2; element 3 is an illumination ring implemented with a plurality of illumination sources 30, such as light emitting diodes (LEDs), arranged so as to emit light towards imaging target 1; element 4 is a further polarizer, also referred to herein as detection polarizer 4, with a polarization orientation orthogonal to that of source polarizer 2; element 5 is an optical filter, or filter 5; and element 6 is one or more lenses, for magnification of the area being imaged. As can be appreciated, to the extent magnification is not required, element 6 can be omitted, but for imaging various details of lesions or other skin structures, a magnification typically of 10× or more is desirable.

Generally, in operation, at least some of the light emitted from illumination element 3 towards imaging target 1 is reflected from target 1 back through elements 4-6 onto image capture element 7. As shown in FIG. 1, illumination element 3 is implemented with two concentric rings of light emitting diodes (LEDs): an inner ring of LEDs emitting white (broad-spectrum) light, and an outer ring of LEDs, a subset of which emit white light and another subset of which emit visible light of a narrow band of wavelengths, such as blue light centered about a wavelength of 400 nm, +/−20 nm. As shown in FIG. 1, the subset of blue light emitting LEDs of the outer ring is arranged in four pairs of LEDs radially spaced at intervals of approximately 90 degrees relative to each other. The subset of white light emitting LEDs of the outer ring is arranged in four groups of six LEDs each arranged between the blue LEDs.

As shown in FIG. 1, source polarizer 2 is generally annular in shape and is arranged proximate to illumination element 3 so as to polarize light emitted from the white light emitting LEDs of the outer ring of illumination element 3. Source polarizer 2 has an inner opening that is large enough so that light emitted from the inner ring of white light emitting LEDs of illumination element 3 is not polarized by polarizer 2. Furthermore, polarizer 2 is provided with openings or notches corresponding to the locations of the blue light emitting LEDs of the outer ring of illumination element 3 so as not to polarize the blue light emitted therefrom.

In exemplary implementations, the blue LEDs of the outer ring, the white LEDs of the outer ring and the white LEDs of the inner ring are configured as three independently activatable groups of LEDs, which can be respectively activated in accordance with the three imaging modes mentioned above. More specifically, in the first mode of operation, only the LEDs of the inner ring of illumination element 3 are activated so as to provide unpolarized white light illumination of the imaging target 1, an image of which can be captured by image sensor 7 via elements 4-6. In the second mode of operation, only the white LEDs of the outer ring of illumination element 3 are activated, so as to provide polarized white light illumination of the imaging target 1, an image of which can be captured by image sensor 7 via elements 4-6. Because the polarization orientations of polarizers 2 and 4 are mutually orthogonal, images captured in this second mode are cross-polarized images.

In the third mode of operation, only the blue LEDs of the outer ring of illumination element 3 are activated, so as to provide unpolarized blue light illumination of the imaging target 1, an image of which can be captured by sensor 7 via elements 4-6. As mentioned above, in the exemplary implementation shown, element 5 is an optical filter, and more specifically, a long-pass optical filter that blocks wavelengths shorter than 420-430 nm. As such, filter 5 blocks the blue light of 380-420 nm emitted from illumination element 3 and reflected from target 1, while passing all light of wavelengths longer than 420-430 nm. Even though long-pass filter 5 will block the shorter blue wavelengths (400-430 nm) it will pass the longer blue wavelengths (>430 nm) so that it will still be possible to capture white-light standard and cross-polarized images (in the other operating modes), in true- or near true-color. Filter 5 can be implemented using, for example, a dichroic filter or an absorption filter, among other possibilities. Filter 5 can also be arranged in other positions, such as between lens element 6 and image capture element 7, or in front of polarizer 4. As can be appreciated, for simplicity of implementation and size considerations, it is preferable that filter 5 be in place in all of the operating modes, as opposed to being selectively movable in and out of the optical path. For arrangements (not shown) in which filter 5 is selectively movable or removable, filter 5 can be moved into the optical path for the blue illumination mode and out of the optical path for the plain and polarized white light modes, so that filter 5 would not affect imaging in those modes.

Figure 2:
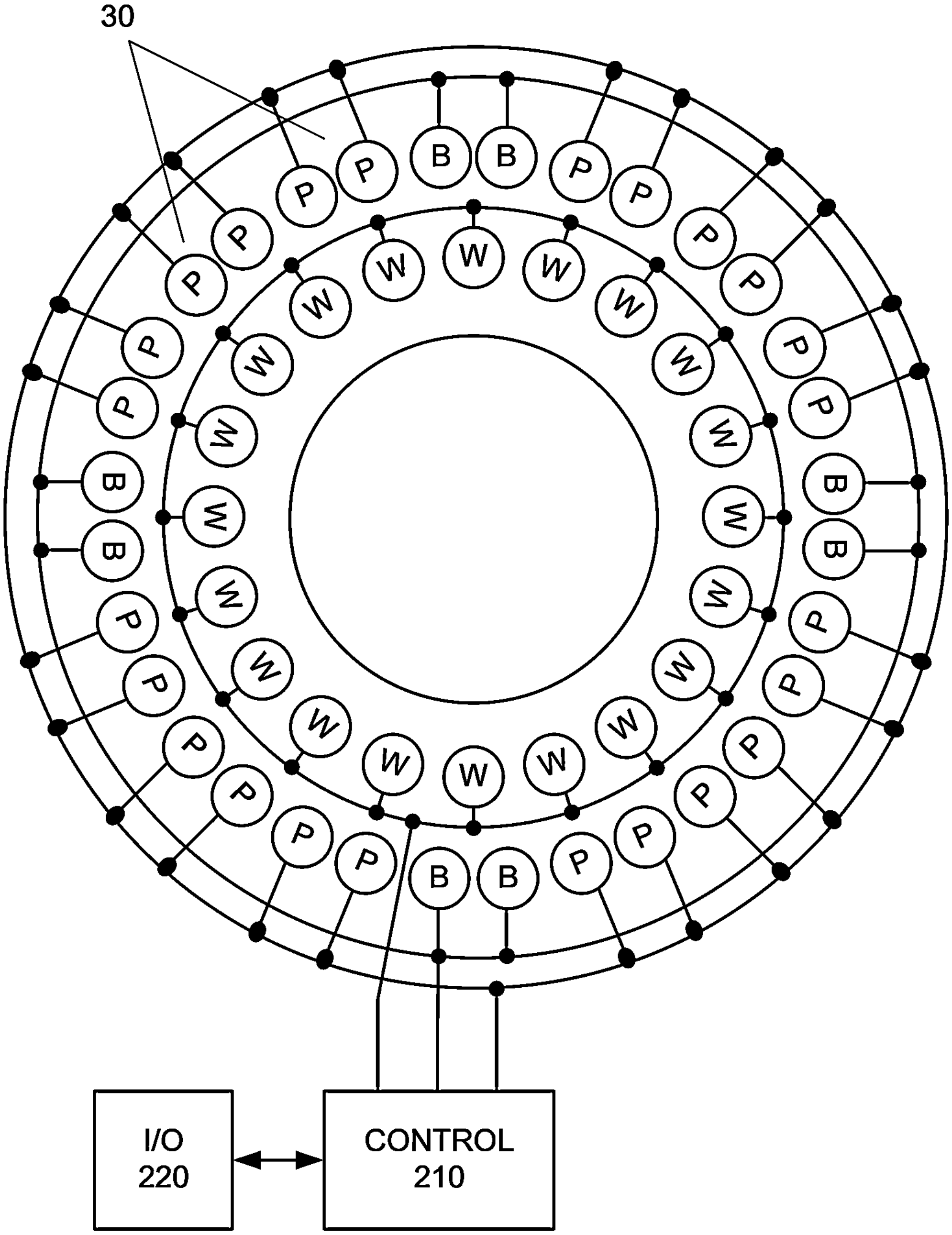
FIG. 2 is a schematic representation of circuitry for an exemplary device in accordance with the present disclosure.

In various implementations, the light sources 30 of illumination element 3 are controlled by control circuitry in accordance with the selected mode of operation. FIG. 2 schematically shows circuitry for controlling the light sources 30 of illumination element 3. As discussed, light sources 30 are arranged in three groups, labeled W (for white light), P (for polarized light), and B (for blue light), and as shown in FIG. 2 are wired accordingly so that each group W, P, B is controlled independently of the other groups by control circuitry 210. Input/output (I/O) circuitry 220, coupled to control circuitry 210, may include buttons, switches, a touchscreen, or the like that a user can actuate to indicate a desired operating mode such as which illumination mode to activate. Based on signal(s) from I/O 220, control circuitry 210 enables the group W, P, B of light sources 30 corresponding to the desired mode of operation. I/O 220 may also include an indicator or display to indicate the selected mode. Control circuitry 210 may include a microcontroller, one or more integrated circuits and/or discrete circuitry. In addition or as an alternative to the above-mention user I/O elements, I/O circuitry 220 may include a data communications interface, such as a wired or wireless serial or parallel interface, or the like. Such an interface can be used to control illumination element 3, including selecting an operating mode, and/or to provide information such as the operating mode or status (e.g., voltage, brightness, usage, error state) of element 3 to an image capture device or system, such as a camera or tablet computer to which a device including element 3 is attached. The image capture device or system can then associate that information with captured images, such as by tagging or labeling the images with the information, or saving the information as image metadata, among other possibilities. As can be appreciated, captured images can be transmitted, stored, and/or processed, such as for analysis by automated systems and methods, and/or users, such as dermatologists, among other possibilities.

Figure 3A:
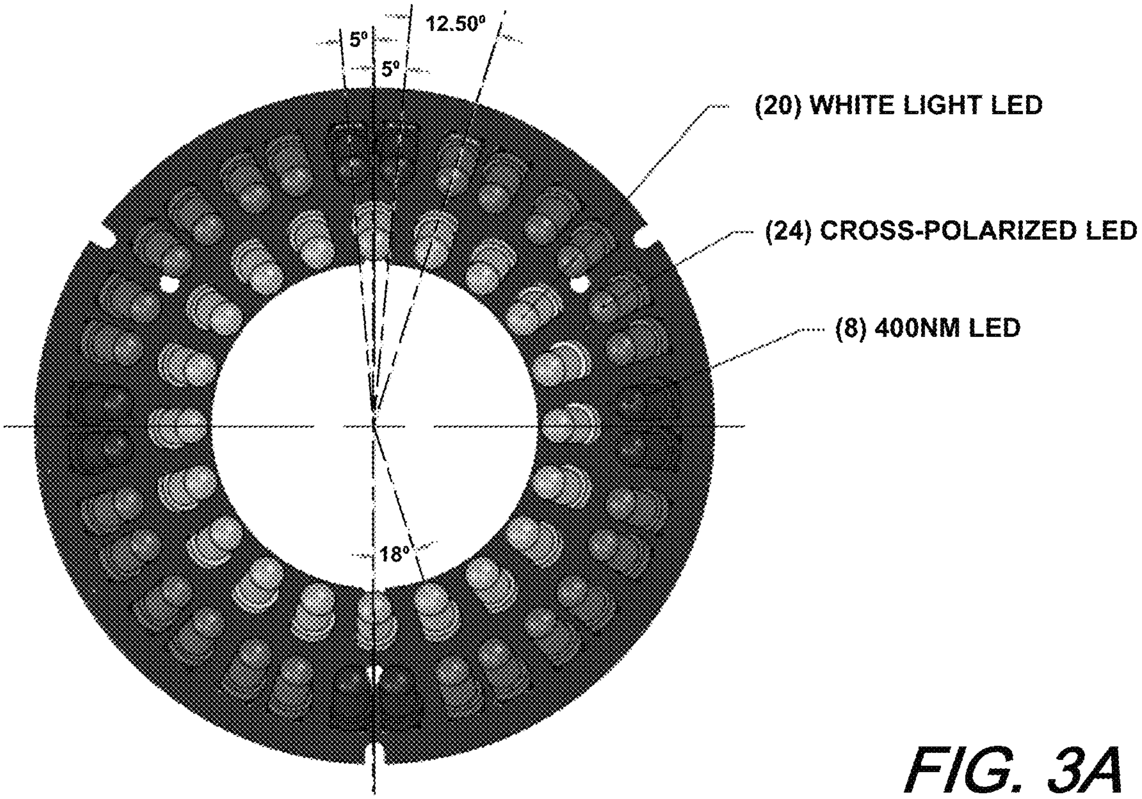
FIGS. 3A and 3B are plan views of exemplary implementations of an illumination element in an exemplary imaging arrangement such as that of FIG. 1.
Figure 3B:
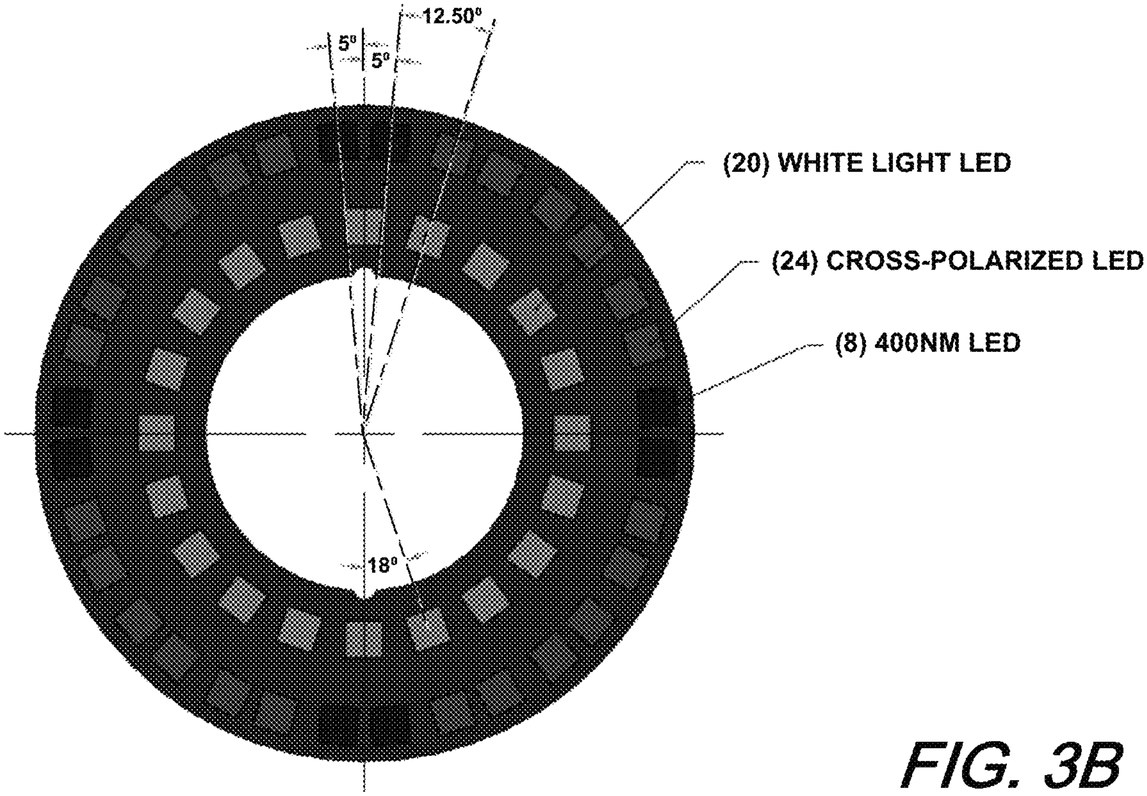
Figure 5:
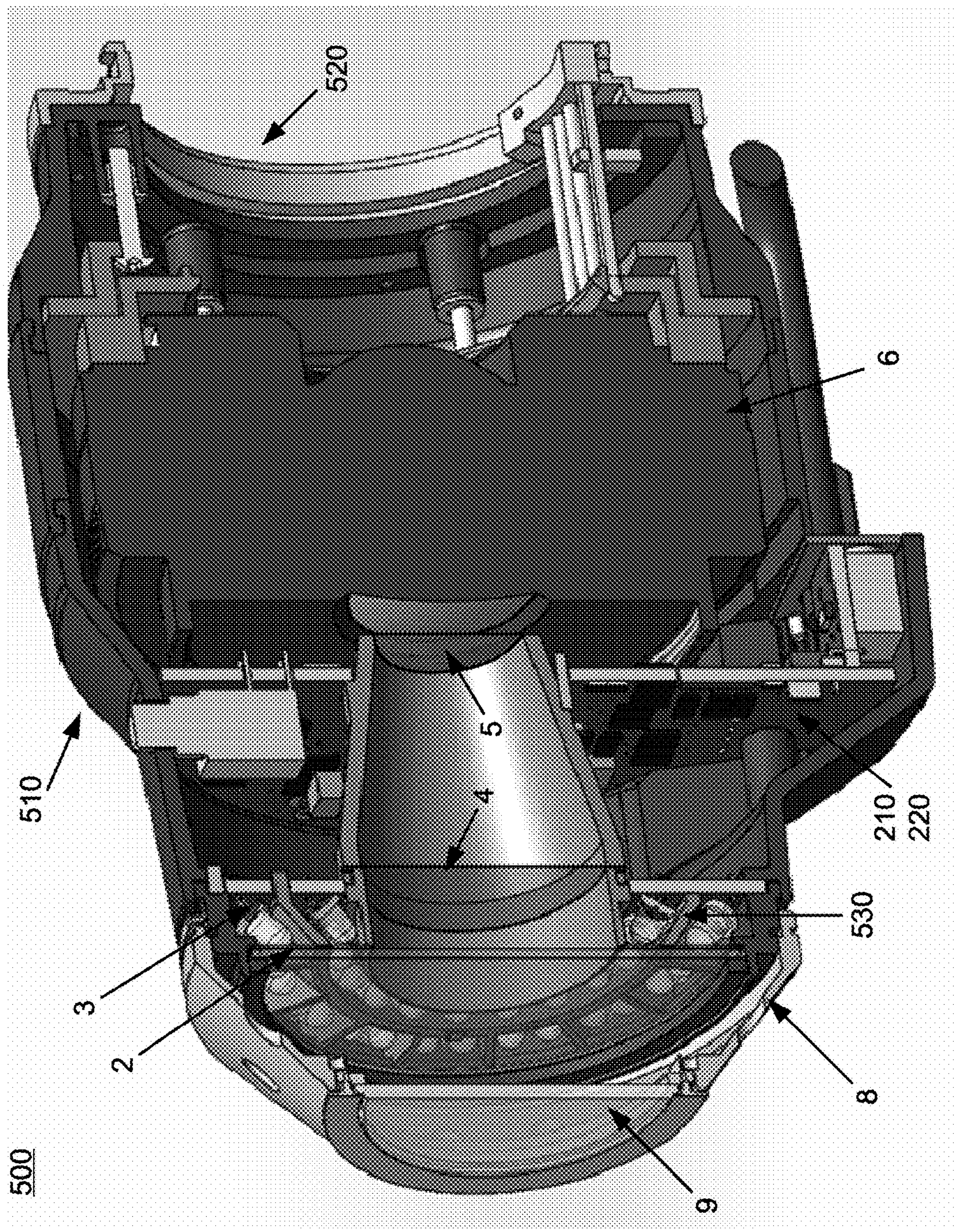
FIG. 5 is a cut-away, isometric view of an exemplary device in accordance with the present disclosure.

FIGS. 3A and 3B are plan views of two exemplary implementations of illumination element 3. In the implementation of FIG. 3A, through-hole LEDs are mounted on a generally annular circuit board, whereas in the implementation of FIG. 3B, surface-mount LEDs are mounted to the surface of a generally annular circuit board. In both implementations, 20 white light emitting LEDs are arranged in an inner ring with a radial angular spacing of 18 degrees between adjacent LEDs. Additionally, in both implementations, 32 LEDs are arranged in an outer ring, in 16 pairs. Adjacent pairs of LEDs are arranged with radial angular spacing therebetween of 12.5 degrees, whereas LEDs of the same pair are arranged with radial angular spacing therebetween of 10 degrees. As mentioned above, four pairs of LEDs emit blue light and are arranged at radial intervals of 90 degrees relative to each other, and the remaining 12 pairs of LEDs emit white light and are arranged between the four pairs of blue LEDs. Other light sources and arrangements thereof are possible, including their number, spacing, and/or grouping, among other parameters. Additionally, arranging an optically opaque barrier between the different groups of light sources can be helpful in reducing or eliminating the bleeding of light emitted from one group to the path taken by light emitted from another group. For example, a barrier between the inner and outer rings of light sources would prevent any light emitted from the inner ring to pass through and be polarized by source polarizer 2. Likewise, a barrier between the blue light sources and adjacent light sources on the outer ring can prevent the blue light from passing through and being polarized by source polarizer 2. An exemplary barrier element 530 is shown in FIG. 5, described below.

The implementation of FIG. 3A allows for mounting the through-hole LEDs angled inward, toward the center of the optical path, thereby helping to maximize the illumination directed to the target 1. Given the typically lower profile of surface-mounted LEDs, the implementation of FIG. 3B allows for placing the polarizer 2 closer to the illumination element 3, and for a more compact arrangement.

As can be appreciated, exemplary implementations of lighting element 3 may have other arrangements of light sources, including a single ring of light sources or more than two rings of light sources. Furthermore, those light sources configured to emit within a narrow band of wavelengths, such as blue, can be implemented with devices such as LEDs that emit such illumination directly, or with broader-band emitting devices such as white-light emitting LEDs, with pass-band filtering arranged so as to filter their emitted illumination to the desired band of wavelengths. As can be appreciated, considerations in determining suitable configurations include the number and sizes of the light sources, and available mounting space (e.g., outer and inner diameters of the annular circuit board of element 3), for example.

Figure 4A:
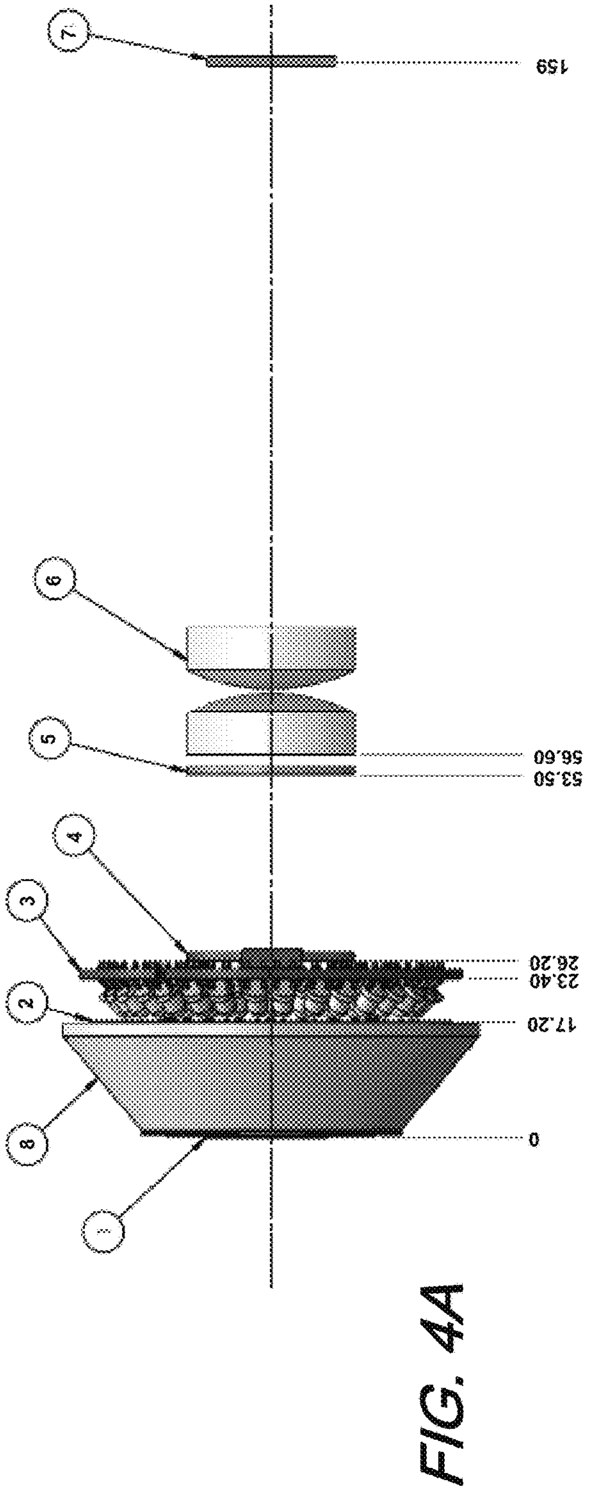
FIGS. 4A and 4B are side views schematically showing the relative spacing of the various elements of arrangements in accordance with the present disclosure.
Figure 4B:
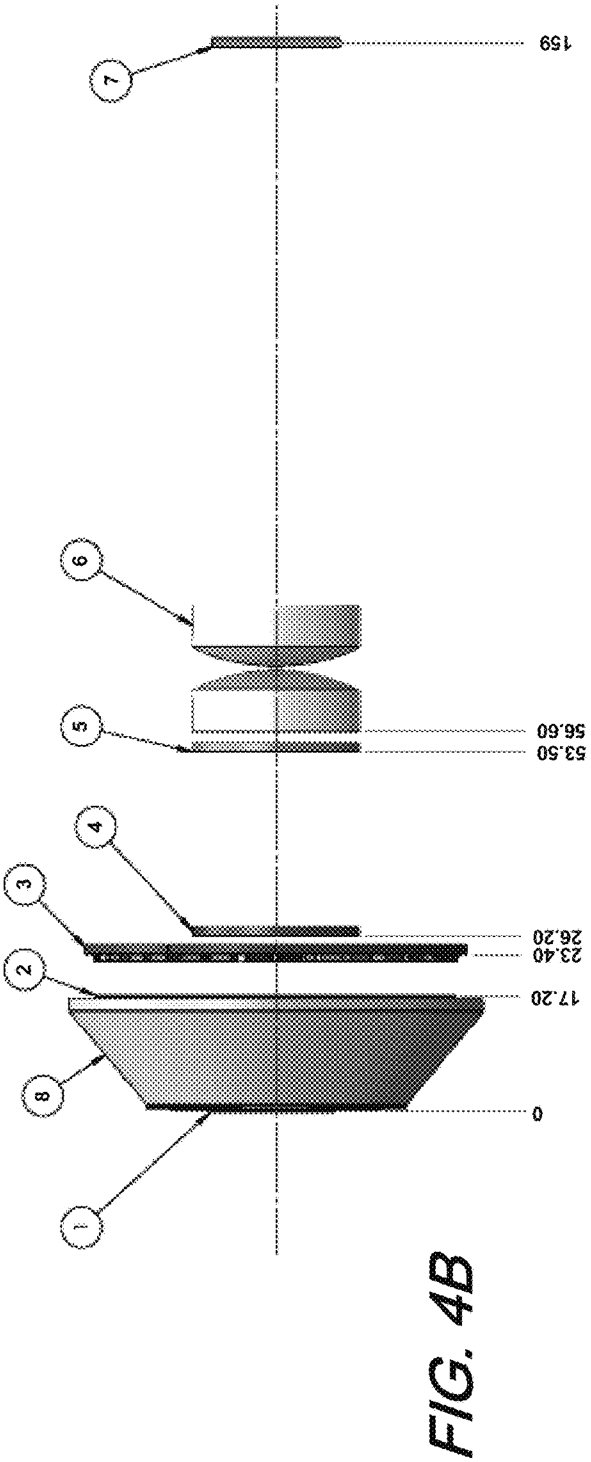

FIGS. 4A and 4B are side views schematically showing the relative spacing of the various elements 1-7 of arrangements in accordance with the present disclosure. FIG. 4A shows the case in which the illumination element 3 is implemented with through-hole LEDs, as shown in FIG. 3A. FIG. 4B shows the case in which the illumination element 3 is implemented with surface mount LEDs, as shown in FIG. 3B. In addition to elements 1-7 shown in FIG. 1, FIGS. 4A and 4B also show a spacer element 8 arranged between the target 1 and polarizer 2. Spacer element 8 has a generally frustoconically shaped hollow body with a transparent front contact plate for making contact with target 1.

In various implementations, elements 2-5 may be arranged in a housing adapted for attachment to a camera, with elements 6 and 7 arranged in the camera. As another alternative, elements 2-6 may be arranged in a housing adapted for attachment to a camera having element 7. In another alternative, elements 2-4 and 6 are arranged in a housing for attachment to a camera having image capture element 7, with filter element 5 attached therebetween or arranged in the camera in front of element 7. In yet another alternative, all elements 2-7 may be housed together, such as in a dermatoscope device configured as described herein.

A cut-away, isometric view of a device 500 with one such arrangement in a housing 510 is illustrated in FIG. 5. In addition to elements 2-6, and 8, the arrangement shown in FIG. 5 includes a transparent contact plate 9, removably attached to one end of spacer element 8, which in turn, is removably attached to one end of housing 510. At an opposite end of housing 510, an attachment element 520, such as a bayonet mount or other suitable attachment element, is affixed for attaching the device 500 to a camera, such as a DSLR camera.

Also shown in FIG. 5 is an exemplary barrier element 530 for minimizing or preventing bleeding of light emitted from the various groups of light sources on illumination element 3. Additionally, circuitry such as control circuitry 210 and I/O circuitry 220 discussed above, may be included within housing 510.

As can be appreciated, implementations in accordance with the present disclosure can be made with various arrangements of imaging devices in addition to those implementations described herein. For example, a device can be implemented with additional groups of LEDs and additional polarizer(s) so as to provide a parallel-polarized imaging mode, or modes of various polarizations, among other possibilities. (See, e.g., U.S. patent application Ser. No. 17/010,615, filed Sep. 2, 2020, incorporated herein by reference in its entirety.) In other implementations, light of other wavelengths, such as UV/blue 360-410 nm for example, can be used as illumination. As discussed, filter 5 is provided so as to block the illumination reflected from the target. In exemplary implementations, for illumination wavelengths within the range of visible wavelengths (i.e., 400 to 700 nm for humans, and up to approximately 1,000 nm for some image sensors), filter 5 can include a notch filter with a notch, preferably of a narrow band (e.g., +/−20 nm), matched in wavelength to the illumination, also preferably of a narrow band. In the case red illumination, filter 5 can include a short-pass filter, blocking wavelengths of 700 nm or longer. By thus matching the wavelengths of the narrow-band illumination and the filtering, the amount of narrow-band illumination light reflected from the target and captured by the sensor element 7 is minimized. Additionally, with the filter 5 in place in all of the operating modes (including the plain and polarized white light illumination modes), any color degradation of the white illumination images due to the filter 5 is minimized by using a filter 5 with narrow-band notch filtering, long-pass filtering at the short end the range of visible wavelengths, or short-pass filtering at the long end of the range of visible wavelengths. As can be appreciated, however, filter 5 should be selected so as to avoid blocking or acceptably minimize blocking those wavelengths sought to be detected. Thus, for example, in the case of imaging infrared (IR) or near infrared (NIR) fluorescence, which while not visible to a human can be imaged by some image sensors, a notch filter instead of a short-pass filter 5 would be warranted in implementations for such applications.

In addition to imaging one or more endogenous fluorophores, fluorophores which occur naturally in skin, implementations in accordance with the present disclosure can also be used to image exogenous fluorophores, fluorophores which do not naturally exist in skin, but which can be introduced therein. Several such exogenous fluorophores have been developed which can be injected, topically applied, or ingested as disease markers for enhancing the pathological information in fluorescence images, and for photodynamic therapy applications. Some such exogenous fluorophores approved for human use have excitation wavelengths (e.g., 650-700 nm) in the visible spectrum with IR or NIR emission, which can be imaged by a camera. For example, indocyanine green (ICG), a cyanine dye approved by the US Food and Drug Administration, has been used as a non-targeting contrast agent for optical imaging. ICG absorbs mainly between 600 nm and 900 nm and emits fluorescence between 750 nm and 950 nm. Fluorescein, which is commonly used for detecting corneal or vessel abnormalities and whose applications also extend to bioimaging of whole anatomic structures and even further to cellular components in immuno-histological staining, has an excitation peak at 498 nm and an emission peak at 517 nm. Thus, for imaging fluorescein for example, a group of light sources of illumination element 3 is preferably provided to emit narrow-band light of 498 nm, and filter 5 is preferably implemented with a narrow-band notch filter having a notch at 498 nm.

In further exemplary implementations of devices in accordance with the present disclosure, multiple fluorophores, endogenous and/or exogenous, with different excitation illumination wavelengths can be imaged. In such implementations, in addition to or instead of the white light emitting light sources, illumination element 3 may include two or more independently activatable groups of light sources which emit illumination of two or more (preferably narrow) wavelength bands, respectively. Alternatively, or additionally, illumination element 3 may include electrically tunable light sources, whose illumination wavelength can be varied so as to emit illumination of various wavelengths to excite different fluorophores, without requiring the inclusion of additional light sources with fixed wavelengths. Also, filter 5 can be implemented with two or more cascaded filters, for example, to respectively block the reflected illumination of the two or more wavelength bands emitted from element 3.

In further exemplary implementations, illumination element 3 can be implemented with a further group of narrow-band illumination sources arranged (such as in the outer ring between the white-light emitting sources or next to the narrow-band illumination sources of the other group) so that light emitted therefrom is polarized by source polarizer 2. Cross-polarized, narrow-band illumination can be useful for absorption imaging of a compound having a characteristic absorption peak to which the illumination is matched. In performing absorption imaging of a particular compound, cross-polarized illumination of a narrow-band matching the absorption characteristics of the compound is shone onto the skin. Areas in which the compound is present will appear darker compared to their surroundings. The use of cross-polarization blocks imaging the illumination reflected off of the surface of the skin, which would otherwise obscure the darker areas representative of the absorbing compound. For performing such absorption imaging, detection filtering 5 may be omitted, or if so configured, selectively removed from the imaging optical path. If, however, the further narrow-band illumination used for such absorption imaging is of a sufficiently different wavelength so as not to be blocked thereby, or acceptably minimally blocked thereby, filter 5 can remain in place.

In further exemplary implementations capable of absorption imaging, source polarizer 2 can be implemented so as to polarize light emitted by the one or more groups of light sources which emit narrow-band illumination. This can be done, for example, by implementing source polarizer 2 as an annular ring without notches or openings corresponding to said light sources, or by providing an additional source polarizer for said light sources, if a different polarization orientation is desired. As discussed, for such absorption imaging, however, detection filtering 5 can be omitted or removed from the imaging optical path, or selected so as to avoid or acceptably minimize any blocking of the reflected narrow-band illumination used for such imaging.

As can be appreciated, absorption imaging for more than one compound can be implemented by providing polarized narrow-band illumination for two or more bands corresponding to the absorption spectral characteristics of two or more compounds.

It should be noted that for implementations for which polarized narrow-band illumination is not required, it is preferable not to polarize the narrow-band illumination because the polarizer will typically attenuate the illumination to some degree. Moreover, some polarizers can add a color cast depending on their construction. If polarized narrow-band illumination is used, it may be desirable to increase the brightness of the illumination to compensate for any attenuation, and to use a polarizer which adds no or acceptably minimal color cast.

In further exemplary implementations, source polarizer 2 and/or detection polarizer 4 can be implemented as electrically tunable linear polarizers, whose polarization orientations can be varied electrically, such as with signals generated by control circuitry 210.

Figure 6:
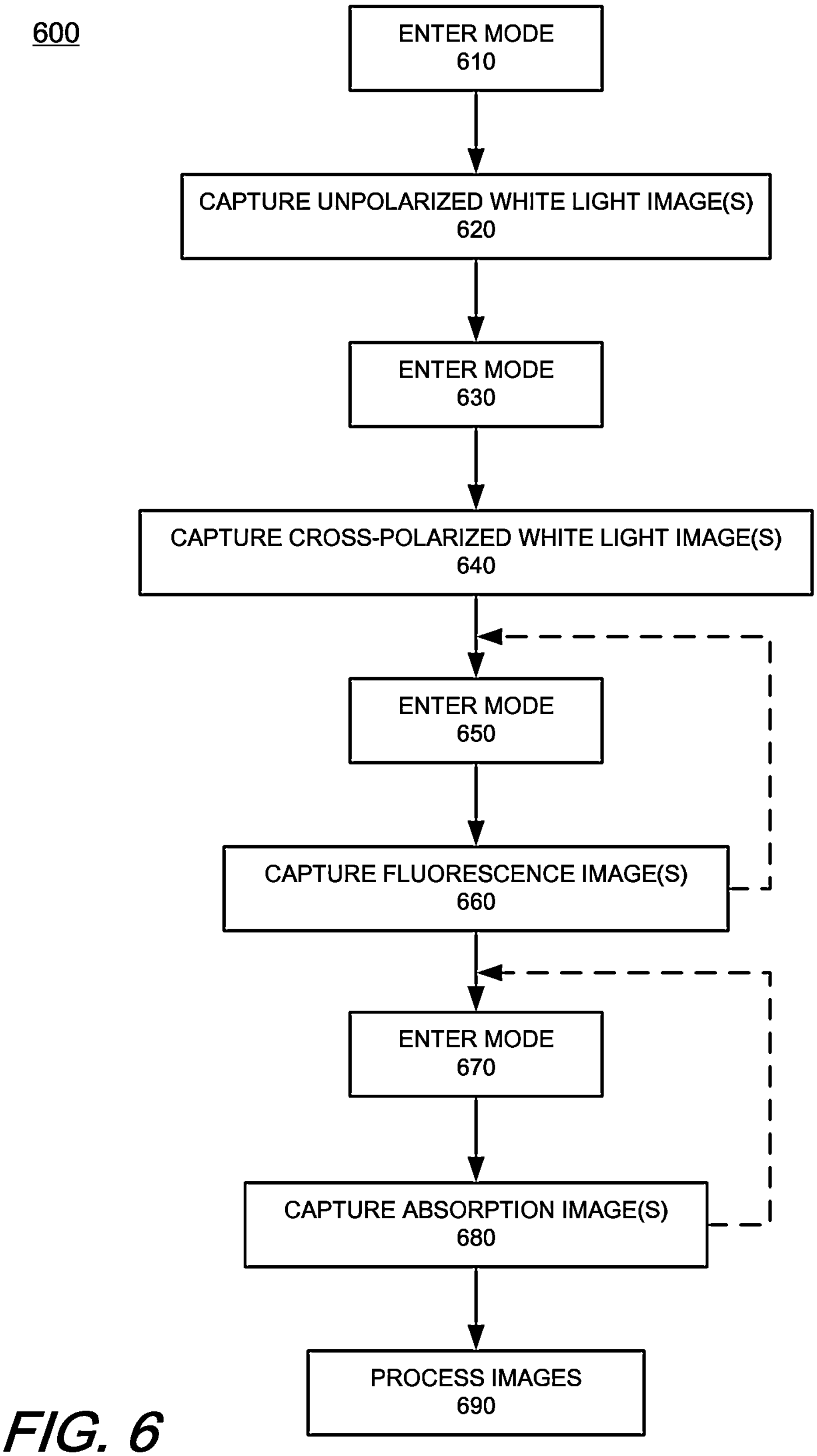
FIG. 6 is a flowchart of an exemplary method in accordance with the present disclosure.

An exemplary method relating to imaging devices such as described, will now be described with reference to FIG. 6, which shows a flowchart depicting an exemplary process 600. As shown in FIG. 6, operation begins at 610 in which one of the modes of operation described above is entered, such as by default upon initialization, or by user selection. For purposes of this description, it is assumed the unpolarized white light image mode, in which the device emits unpolarized white light, is entered at 610. Operation then proceeds to 620, in which one or more unpolarized white light images are captured, such as with a DSLR camera to which the device is attached. At 630, a second mode is entered, such as the cross-polarized white light mode, and at 640 one or more cross-polarized white light images are captured. At 650, a third mode is entered, such as the fluorescence blue light mode, and at 660 one or more fluorescence blue light images are captured. With an imaging device capable of imaging multiple fluorophores, as described herein, operations 650, 660 may be repeated multiple times, as one or more image of each fluorophore is captured with different narrow-band illumination in each fluorescence imaging mode. Additionally, with an imaging device capable of absorption imaging, as described herein, an absorption imaging mode can be entered at 670 and one or more absorption images captured at 680. With an imaging device capable of absorption imaging multiple compounds, operations 670, 680 may be repeated multiple times, as one or more absorption image for each compound is captured with different narrow-band illumination in each absorption imaging mode.

As can be appreciated, the selection of modes and the order in which they are entered, as described, are merely illustrative; the user can select a different order and set of modes, or a single mode. Preferably, the various images are captured in temporal proximity to each other, without moving the device or target imaged area between images so as to avoid or minimize the effects of any movement.

With the various images having been captured, operation then proceeds to 690, in which processing of the images is carried out. Processing at 690 may include, for example, performing registration of two or more images, and adjusting color and/or intensity levels of the images to ensure that they are similar in color and intensity. Additionally, with more diffuse reflectance, images may become soft and thus sharpening them may be desirable. Also, it may be desirable to compensate for the loss of light at the greater depths imaged with cross-polarization due to absorption and scattering away from the camera. Accordingly, sharpening and/or intensity compensation using known techniques preferably can be applied, if warranted, in processing 690.

Operations in processing 690 may also include image subtraction or blending to highlight the differences and/or similarities between images.

Alternatively or additionally, processing 690 may include performing feature detection on images captured with different modalities in order to detect feature(s) of interest, such as pigmented lesions. Feature detection may include a variety of techniques, including performing a binary image segmentation procedure in which those image pixels representing detected features are turned white, while the remaining pixels representing background tissue are turned black. Logical operations, such as AND or XOR operations, can then performed on these binary images to enhance various features.

Further processing may include modifying one or more of the images to highlight features of interest. This may include generating indicia and overlaying them onto the image(s), among other possibilities.

In addition or as an alternative to generating images based on the captured images, processing 690 may include determining various measurements and/or metrics such as the size, area, shape, symmetry, and coloration of lesions and fluorescing structures, or the shape and distribution of blood vessels, among other possibilities. Both image and numerical information thus determined can be compared to information from images captured at a different time, such as to determine the efficacy of treatment or disease progression, for example, with further metrics determined based on such differential analysis, among other possibilities.

It should be noted that some aspects of method 600 can be performed automatically, such as under program control, while others can be performed manually. For example, depending on the imaging apparatus used, several implementations of which are described herein, the entry of modes (at 610, 630, 650, 670) can be done with user interaction with the apparatus, or can be done automatically, under program control.

Figure 7A:
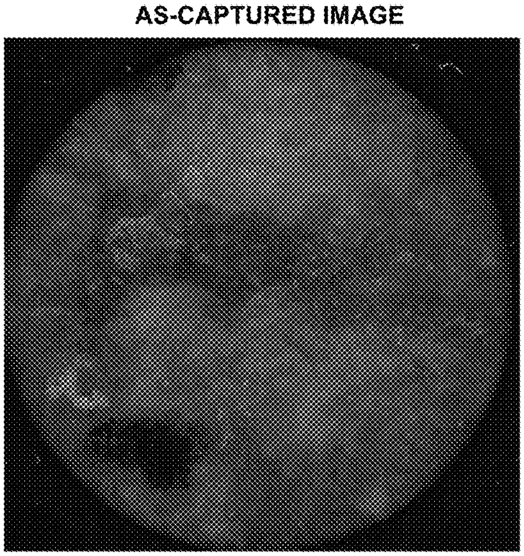
FIG. 7A shows an as-captured RGB image with blue illumination of a target area of skin and FIG. 7B shows the image of FIG. 7A with the blue channel removed.
Figure 7B:
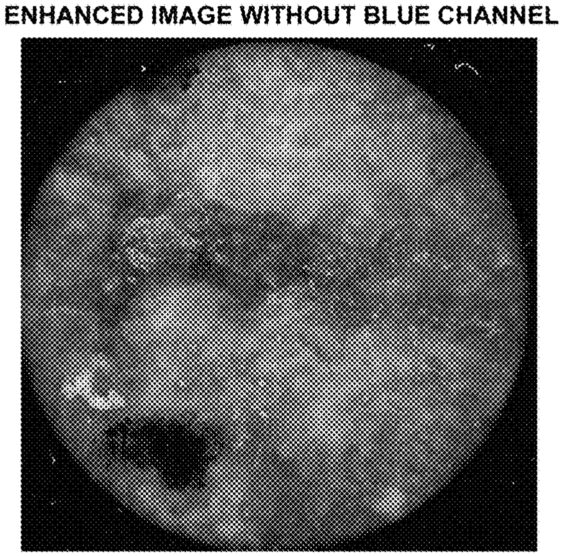
Figure 8A:
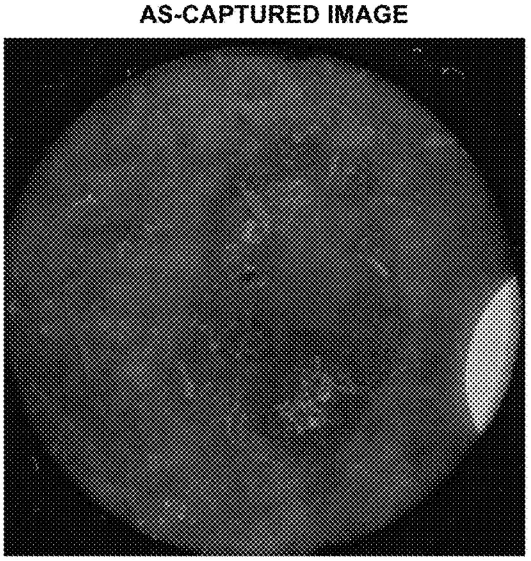
FIG. 8A shows an as-captured RGB image with blue illumination of a target area of skin and FIG. 8B shows the image of FIG. 8A with the blue channel removed.
Figure 8B:
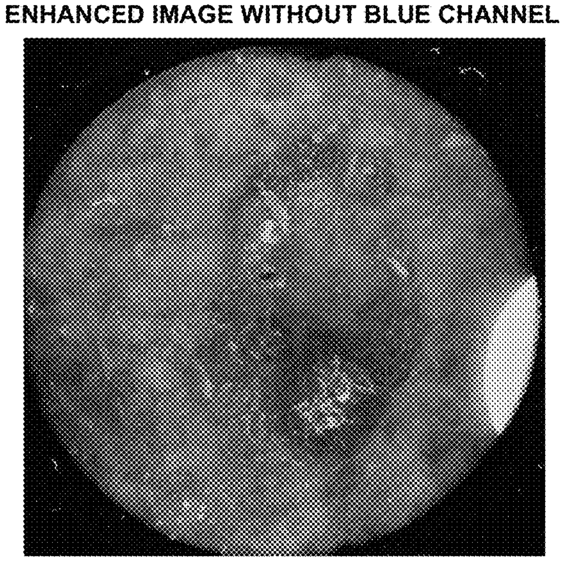
Figure 9A:
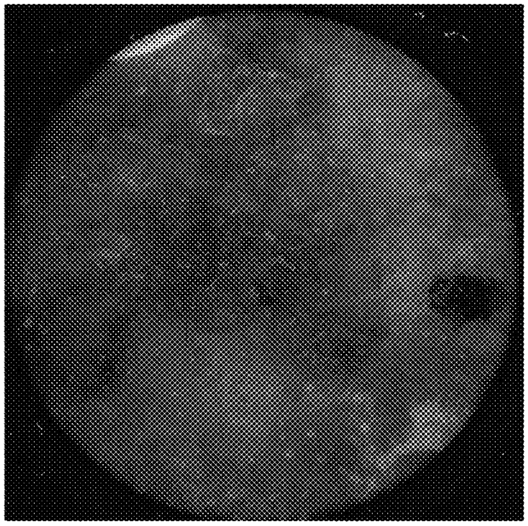
FIG. 9A shows an as-captured RGB image with blue illumination of a target area of skin and FIG. 9B shows the image of FIG. 9A with the blue channel removed.
Figure 9B:
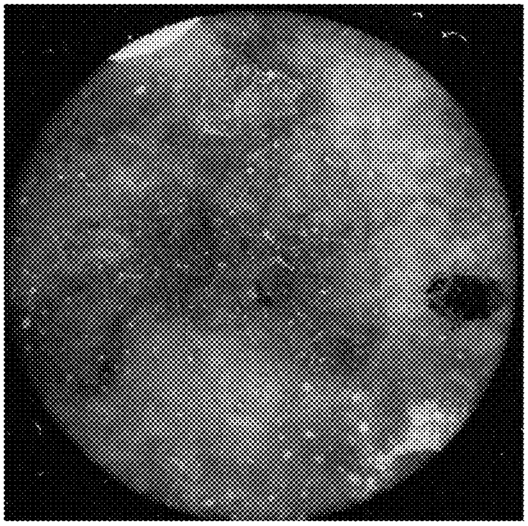
Figure 10A:
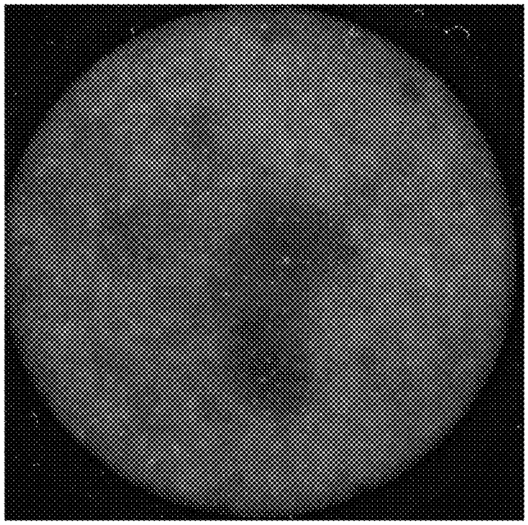
FIG. 10A shows an as-captured RGB image with blue illumination of a target area of skin and FIG. 10B shows the image of FIG. 10A with the blue channel removed.
Figure 10B:
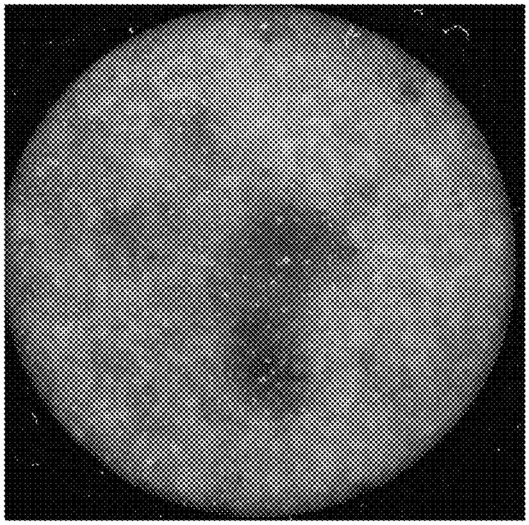

Furthermore, images captured with the blue light, for example, may be post-processed for better visualization of the fluorescence from the imaged skin. Such processing may entail, for example, isolating individual color channels, or removing the blue (B) color channel from the captured RGB image and enhancing the green (G) and red (R) color channels. FIG. 7A shows an as-captured image with blue illumination of a target area of skin. FIG. 7B shows an image that results from applying the aforementioned processing to the image of FIG. 7A. FIGS. 8A-10B show additional pairs of such images for other target areas. It should be noted that the images of FIGS. 7A, 8A, 9A, and 10A, were captured without filter 5 to block the blue illumination reflected from the imaged area of skin.

White light standard images and cross-polarized images captured as described may be processed such as by performing color/white-balance correction, among other processing. Such correction may be desirable given the blocking of the shorter blue wavelengths by filter 5. Additionally, for cross-polarized images, processing 690 may include removing the green and red channels for better visualization of melanin, useful for assessing conditions such as vitiligo. The resulting image would look similar to an image observed under Wood's lamp illumination.

Processing 690 may also include displaying, storing, and/or communicating the images as captured or processed, and/or further images, measurements, and/or metrics derived from the images.

Figure 11:
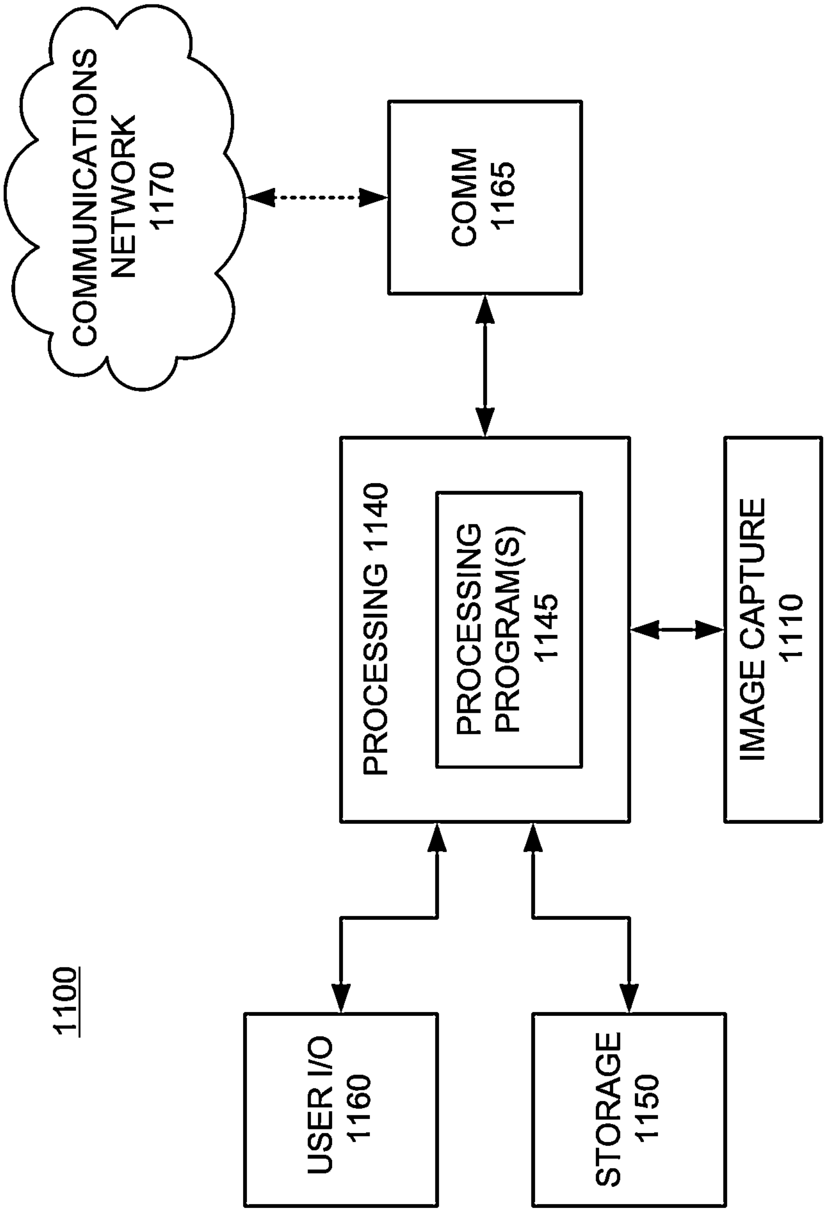
FIG. 11 is a schematic representation of an exemplary system in accordance with the present disclosure.

Turning now to FIG. 11, there is shown in schematic form an exemplary imaging system 1100 in accordance with the present disclosure. As shown in FIG. 11, components of system 1100 include an image capture apparatus 1110 coupled to processing circuitry 1140. Image capture apparatus 1110 may include, for example: a device 500 such as described above, attached to a camera; a dermatoscope with image capturing capabilities, such as Canfield Scientific Inc.'s VISIOMED D200EVO and VEOS DS3 devices modified to provide the various modes of imaging as described herein; or a mobile device with image capturing capabilities, such as a smartphone or tablet computer, with attachment(s) for providing imaging as described herein, among other possibilities.

The captured images can be single mode or multimodal, including, for example, all or a subset of the modalities described herein.

Images captured by image capture apparatus 1110 are provided to processing circuitry 1140 for processing as described above. Processing circuitry 1140 may also control image capture apparatus 1110, for example, by controlling one or more aspects of the image capture and/or illumination of the subject, such as exposure, and modality, including, for example, which illumination mode to use, among others.

Images may also be provided to processing circuitry 1140 from other sources and by other means. For example, images may be provided via communications network 1170, or in a non-transitory storage medium, such as storage 1150.

Processing circuitry 1140 may be coupled to storage 1150, for storing and retrieving images, among other data, and/or programs, software, and firmware, among other forms of processing instructions; and to input/output devices 1160, such as a display device and/or user input devices, such as a keyboard, mouse, touchscreen, or the like. Processing circuitry 1140 may also be coupled to communications circuitry 1165 for interconnection with a communications network 1170, such as a local network and/or the Internet, for transmitting and receiving images and/or data, and/or receiving commands, software updates or the like. Processing circuitry 1140, storage 1150, I/O 1160, and/or communications module 1165 may be implemented, for example, with one or more computers, workstations, processors, or the like, operating in accordance with one or more programs 1145 embodied in a compatible, non-transitory, machine-readable storage medium. Program(s) 1145 may be stored in storage 1150 and/or other memory devices (not shown), and provided therefrom and/or from communications network 1170, via communications module 1165, to processing circuitry 1140 for execution. Methods in accordance with the present disclosure, such as method 600 described above with reference to FIG. 6, can be implemented by execution of one or more programs 1145.

The various components of system 1100 may be connected via any suitable wired or wireless connections.

It should be noted that the exemplary system 1100 illustrates just one of a variety of possible arrangements contemplated by the present disclosure. For example, the various components of system 1100 need not be co-located. For instance, image capture apparatus 1110 and I/O devices 1160 can be located in a practitioner's office and processing circuitry 1140 and storage module 1150 can be remotely located, functioning within a telehealth framework, or can be "cloud-based," interacting with image capture apparatus 1110 and I/O devices 1160 over communications network 1170. In other exemplary arrangements, I/O devices 1160 can be remotely located from image capture apparatus 1110, thereby allowing a user to remotely examine subjects' images, such as in a telehealth arrangement.

In other implementations, system 1100 can be implemented with a portable or mobile computing device having image capture apparatus 1110 integrated therein, such as a tablet computer, smartphone, a Canfield VEOS DS3 device, or the like, modified or provided with attachment(s) to provide imaging as described herein.

The foregoing merely illustrates principles of the present disclosure and it will thus be appreciated that those skilled in the art will be able to devise numerous alternative arrangements which, although not explicitly described herein, embody the principles of the present disclosure and are within its spirit and scope. For instance, as can be appreciated, a variety of arrangements of processing and imaging systems and devices are contemplated consistent with the present disclosure. Additionally, although illustrated as single elements, each block or step shown may be implemented with multiple blocks or steps, or various combinations thereof. Also terms such as "software," "application," "program," "firmware," or the like, are intended to refer, without limitation, to any instruction or set of instructions, structure, or logic embodied in any suitable, non-transitory, machine-readable medium. It is to be understood that numerous modifications may be made to the illustrative embodiments and that other arrangements may be devised without departing from the spirit and scope of the present invention as defined by the appended claims.

What is claimed is:

1. A tissue imaging apparatus comprising:
- an optical opening;
- a plurality of light sources including three groups of light sources arranged about the optical opening, wherein first and second groups of light sources are configured to emit white light, and a third group of light sources is configured to emit light of a first band of wavelengths narrower than a band of wavelengths of visible light;
- a detection polarizer configured to polarize light passing through the optical opening;
- a detection filter configured to filter light passing through the optical opening, the detection filter being configured to block light of the first band of wavelengths and to pass light of at least near true color; and
- a source polarizer configured to polarize light emitted from the first group of light sources, wherein the white light emitted from the tissue imaging apparatus by the second group of light sources is unpolarized.

2. The apparatus of claim 1, wherein an orientation of polarization of the detection polarizer and an orientation of polarization of the source polarizer are mutually orthogonal.

3. The apparatus of claim 1, wherein the plurality of light sources includes a fourth group of light sources configured to emit light of a second band of wavelengths narrower than the band of wavelengths of visible light.

4. The apparatus of claim 3, wherein the detection filter is configured to block light of the second band of wavelengths.

5. The apparatus of claim 3, wherein the source polarizer is configured to polarize light emitted from at least one of the third or fourth groups of light sources.

6. The apparatus of claim 1, wherein the light sources of the same group are evenly distributed about the optical opening.

7. The apparatus of claim 1 comprising circuitry configured to activate one group of light sources at a time.

8. The apparatus of claim 1, wherein the first band of wavelengths is in a band of 380 nm through 420 nm.

9. The apparatus of claim 1, wherein the detection filter includes at least one of a long-pass, short-pass, band-pass, or notch optical filter.

10. The apparatus of claim 1, wherein the detection filter is configured to selectively filter light passing through the optical opening.

11. The apparatus of claim 1 comprising an image capture device configured to capture an image through the optical opening.

12. A skin analysis system comprising the apparatus of claim 1, wherein the tissue is skin.

13. A tissue imaging method comprising:

illuminating a tissue with polarized white light emitted from a first group of light sources arranged about an optical opening of a tissue imaging apparatus;

illuminating the tissue with unpolarized white light emitted from a second group of light sources arranged about the optical opening;

illuminating the tissue with light of a first band of wavelengths narrower than a band of wavelengths of visible light, said light emitted from a third group of light sources arranged about the optical opening;

polarizing light passing through the optical opening; and filtering light passing through the optical opening so as to block light of the first band of wavelengths and to pass light of at least near true color.

14. The method of claim 13, wherein an orientation of polarization of the polarized white light and an orientation of polarization of the polarized light passing through the optical opening are mutually orthogonal.

15. The method of claim 13 comprising illuminating the tissue with light of a second band of wavelengths narrower than the band of wavelengths of visible light, said light emitted from a fourth group of light sources arranged about the optical opening.

16. The method of claim 15, wherein the filtering blocks light of the second band of wavelengths.

17. The method of claim 13, wherein one group of light sources is activated at a time.

18. The method of claim 13, wherein the first band of wavelengths is in a band of 380 nm through 420 nm.

19. The method of claim 13, wherein the filtering includes at least one of a long-pass, short-pass, band-pass, or notch optical filtering.

20. A non-transitory computer-readable storage medium having stored thereon instructions for causing a system to:

illuminate a tissue with polarized white light emitted from a first group of light sources arranged about an optical opening of a tissue imaging apparatus;

illuminate the tissue with unpolarized white light emitted from a second group of light sources arranged about the optical opening;

illuminate the tissue with light of a first band of wavelengths narrower than a band of wavelengths of visible light, said light emitted from a third group of light sources arranged about the optical opening;

polarize light passing through the optical opening; and filter light passing through the optical opening so as to block light of the first band of wavelengths and to pass light of at least near true color.

* * * * *